United States Patent [19]

Quakenbush

[11] Patent Number: 5,099,079
[45] Date of Patent: Mar. 24, 1992

[54] PROCESS FOR SEPARATING ACID FROM NITRO SUBSTITUTED AROMATICS USING A MOLTEN NITRATE SALT

[75] Inventor: Allen B. Quakenbush, Lake Charles, La.

[73] Assignee: Olin Corporation, Cheshire, Conn.

[21] Appl. No.: 559,970

[22] Filed: Jul. 26, 1990

[51] Int. Cl.$^5$ ............................................. C07C 205/11
[52] U.S. Cl. ..................................... 568/934; 568/940; 568/939; 568/935; 568/932; 568/928; 210/633
[58] Field of Search ................. 210/633; 568/934, 940, 568/939, 935, 932, 928

[56] References Cited

U.S. PATENT DOCUMENTS 2,362,743  11/1944  Crater ................................. 568/934
4,804,792  2/1989   Mason et al. ....................... 568/939
4,918,250  4/1990   Mason et al. ....................... 568/934

Primary Examiner—Deborah L. Kyle
Assistant Examiner—Valerie Fee
Attorney, Agent, or Firm—Gregory S. Rosenblatt; Paul Weinstein

[57] ABSTRACT

Described herein is a process for separating an acid impurity from a solution containing acid and a nitro substituted aromatic compound by contacting the solution with at least one molten nitrate salt.

25 Claims, No Drawings

PROCESS FOR SEPARATING ACID FROM NITRO SUBSTITUTED AROMATICS USING A MOLTEN NITRATE SALT

FIELD OF THE INVENTION

This invention relates to a process for separating an acid impurity from a solution containing the acid and a nitro substituted aromatic compound, which process comprises contacting the solution with a molten nitrate salt.

BACKGROUND OF THE INVENTION

Nitro substituted aromatic compounds, which include nitrotoluenes such as mononitrotoluene and dinitrotoluene, are generally commercially produced by the nitration of the corresponding aromatic hydrocarbon. The nitration reaction is typically carried out by reacting the aromatic hydrocarbon with nitric acid in the presence of sulfuric acid, or with nitric acid alone. Examples of such nitration reactions are illustrated in the following patents:

U.S. Pat. No. 2,362,743 describes the preparation of dinitrotoluene by the nitration of toluene with nitric acid of about a 70% concentration to produce mononitrotoluene, followed by further nitration with nitric acid of about 98% concentration to produce a crude dinitrotoluene. This patent states that the use of the concentrated nitric acid is an improvement over the use of sulfuric acid alone and mixtures of sulfuric and nitric acids as nitrating agents. The crude dinitrotoluene produced by the process of the patent is stated to be subjected to several steps of washing, neutralizing, alcohol treatment, and centrifuging to obtain the 2,4-dinitrotoluene.

U.S Pat. No. 4,804,792 describes the nitration of benzene and toluene by contacting these with concentrated nitric acid in the presence of a molten nitrate salt. The patent states that the molten salt serves as a temperature regulator for the reaction and as an isothermal medium for the reactants. A preferred method of contacting the reactants in the presence of the molten salt is stated to be by bubbling the reactants into a bath of the molten salt by means of a carrier gas such as nitrogen. The desired product is stated to be separated out by a variety of well known procedures.

U.S. Pat. No. 4,918,250 describes a process for nitrating toluene to DNT and phase separation of the product using an inorganic salt as a phase separation agent. In this patent, DNT is produced in a two-step liquid phase nitration reaction between nitric acid and toluene in the absence of sulfuric acid and solvent. In the process of the patent, the inorganic salt is incorporated into the mixture of DNT and unreacted nitric acid in an amount sufficient to cause phase separation of the mixture in order to facilitate isolation of the DNT from the unreacted nitric acid in the product mixture (column 2, lines 27 to 33). After phase separation, the patent states that washing with water and a basic solution produces a purified DNT (column 3, lines 13 to 15).

The processes discussed, as well as commercial processes nitrate the aromatic compound with a strong acid to produce a nitro substituted aromatic compound. A separation step is required to separate the acid from the product. The crude product is generally washed with water and dilute alkaline solutions. The spent wash solution is then treated before discharge or recycle to the nitration process. If process by-products are present, their separation is more difficult by the bulk of the water. The large quantity of water used requires excessive energy to recover the by-products by distillation. Further, the product nitro substituted aromatic compound is still generally contaminated with the acid.

To be commercially usable for many applications the nitro substituted aromatic compound must have an acid content of less than 3%. For example, DNT is useful as an intermediate for producing toluene diisocyanate (TDI). This requires that the contaminant acid must be essentially completely removed. The techniques described above which utilize large amounts of water and an alkaline solution do not completely separate all of the acid from the product.

Accordingly, alternate separation means would be desirable to remove essentially all of the acid contained in the product nitro substituted aromatic compound.

THE INVENTION

The present invention is directed to a process for separating acid impurities from a solution containing the acid and nitro substituted aromatic compounds, particularly nitrotoluenes such as mononitrotoluene and dinitrotoluene. The method comprises contacting the solution containing the acid and nitro substituted aromatic compound with at least one molten nitrate salt.

The present method reduces the amount of water needed for washing the crude solution containing the acid and nitro substituted aromatic compound. Additionally, the present invention reduces the quantity of alkali used in conventional separation processes to neutralize the crude acidic solution prior to biological treatment, and subsequent discharge into the environment.

The molten nitrate salt is not miscible with the acidic solution containing the nitro substituted aromatic compound, so that when they are contacted two layers are formed. The contaminant acid in the crude solution is transferred into the molten salt phase, thereby yielding a purer nitro substituted aromatic compound. This is observed by the reduced acidity of the nitro substituted aromatic compound. Since there are two phases, the purified product can be separated from the molten nitrate salt phase by simply decanting or any other suitable separation procedure.

The nitro substituted aromatic compounds which can be treated by the process of this invention include mono-, di-, and trinitrobenzenes, toluenes, and naphthalenes. Preferred nitro substituted aromatic compounds include mono-, di-, and trinitrobenzenes and toluenes.

The molten nitrate salts of this invention include a wide variety of metal nitrates salts which may be in various hydrated states. The preferred nitrate salts have a melting point of about 70° C., with the most Preferred nitrate salts having a melting point below the melting point of the nitro substituted aromatic compound. For example, a typical industrial mixture of DNT isomers has a melting point of about 56° C. Therefore, when treating such a mixture according to the process of this invention, the temperature should be below 56° C. Depending on the nitrate salt mixture selected, temperature as low as about 15° C. can be used. For example a magnesium nitrate hexahydrate-calcium nitrate tetrahydrate eutectic melts at 14.5° C.

Preferred molten nitrate salts include sodium nitrate; potassium nitrate; the calcium nitrate hydrates such as calcium nitrate tetrahydrate; the lithium nitrate hydrates such as lithium nitrate hydrate; the manganese nitrate hydrates such as manganese nitrate tetrahydrate; the magnesium nitrate hydrates such as magnesium nitrate trihydrate, and magnesium nitrate hexahydrate; the zinc nitrate hydrates such as zinc nitrate hexahydrate, and mixtures of one or more of the nitrate salts. A particularly effective molten nitrate salt is a combination of a zinc nitrate hydrate and a magnesium nitrate hydrate, i.e., zinc nitrate trihydrate and magnesium nitrate trihydrate. Minor amounts of other molten metal salts may be included herein as long as the melting point of the molten nitrate salt does not exceed about 70° C.

The molten nitrate salts are used in the process of this invention in amounts of from about 0.1 to about 5.0 parts, preferably from about 0.5 to about 1.5 parts based on the amount 1.0 part, by weight, of nitro substituted aromatic compound.

The crude acidic solutions containing the nitro substituted aromatic compounds are contacted with the molten nitrate salt at a temperature of from about 15° C. to about 130° C., preferably from about 55° C. to about 70° C., for a period of time sufficient to remove essentially all of the acid therefrom, which is typically a time period of from about 1 minute to about 120 minutes.

The crude acidic solutions containing the nitro substituted aromatic compounds which are treated by the process of this invention may be the reaction product of any of the well-known prior art processes. For example, the crude solutions separated herein may be produced by the process described in U.S. Pat. No. 4,918,250, discussed above, which is incorporated herein by reference. This patent describes the preparation of a crude solution containing nitrotoluene by a process which comprises:

(a) reacting toluene with nitric acid having an acid concentration of between about 60 and about 75% by weight based upon the total amount of acid plus water, at a reaction temperature of between about 60° C. and about 75° C., and employing between about 3 and about 5 moles of nitric acid per mole of toluene to produce mononitrotoluene;

(b) reacting said mononitrotoluene with concentrated nitric acid having an acid concentration of between about 90 and about 100% by weight, based upon the total amount of acid plus water therein, at a reaction temperature of between about 40° C. and about 70° C., and employing between about 3 and about 4 moles of concentrated nitric acid per mole of mononitrotoluene to produce a mixture containing dinitrotoluene and unreacted nitric acid; and (c) incorporating an inorganic salt into said mixture to cause phase separation of said dinitrotoluene from said unreacted nitric acid in said mixture.

Alkaline and water washes are then conventionally used to reduce the product acidity. The instant process avoids the use of alkaline and water washes.

Additionally, nitro substituted aromatic compounds produced by reacting an aromatic hydrocarbon with sulfuric acid or mixtures of nitric and sulfuric acids may be treated by the process of this invention.

After contacting the nitro-substituted aromatic compound with the molten salt, the acid containing molten salt can be regenerated by heating to flash off the nitric acid. This can be carried out in a single piece of equipment or the salt can be sent into a nitric acid concentrating unit that employs nitrate salt.

EXAMPLES

The following examples serve to give specific illustrations of the practice of this invention, but they are not intended in any way to limit the scope of this invention.

EXAMPLE 1

A 50/50 mixture of zinc nitrate hexahydrate (250 grams) and magnesium nitrate hexahydrate (250 grams) was melted and partially dehydrated in an oven. The mixture was removed from the oven after a 55.3 gram weight loss which indicated the hydrate state had been reduced from 6 to 4.3. Dinitrotoluene was melted (95 grams) and combined with nitric acid (3.5 grams) and water (1.5 grams). A portion of the prepared molten salt mixture (100 grams) was contacted with the DNT-acid-water mixture. After agitation, the layers were allowed to settle and then separated. Analysis of the organic layer found the DNT acidity had been reduced from the original 3.5% to less than 0.05%.

EXAMPLE 2

A 50/50 mixture of zinc nitrate hexahydrate (50 grams) and magnesium nitrate hexahydrate (50 grams) was melted. Dinitrotoluene was melted (95 grams) and combined with nitric acid (3.5 grams) and water (1.5 grams). The molten salt mixture (100 grams) was contacted with the DNT-acid-water mixture. After agitation, the layers were allowed to settle and then separated. Analysis of the organic layer found the DNT acidity had been reduced from the original 3.5% to 0.28%.

EXAMPLE 3

A 50/50 mixture of zinc nitrate hexahydrate (66.1 grams) and magnesium nitrate hexahydrate (66.1 grams) was melted and partially dehydrated in an oven. The mixture was removed from the oven after a 32.2 grams weight loss. This indicated that the hydrate state had been reduced from 6.0 to 3.0. Nitrobenzene (95 grams) was combined with nitric acid (3.5 grams) and water (1.5 grams). The molten salt mixture (100 grams) was contacted with the nitrobenzene-acid-water mixture. After agitation, the layers were allowed to settle and then separated. Analysis of the organic layer found the nitrobenzene acidity had been reduced from the original 3.5% to 2.0%.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A process for separating an acid impurity from a solution containing the acid and a nitro substituted aromatic compound, which process comprises:

(a) contacting said solution with at least one molten nitrate salt using from about 0.1 to about 5.0 parts of said nitrate salt per each one part by weight of said nitro substituted aromatic compound while maintaining the temperature of said solution substantially at or above the melting point of said nitrate salt; and (b) removing said acid from said solution.

2. A process as defined in claim 1, wherein the aromatic compound is a nitrotoluene.

3. A process as defined in claim 2, wherein the nitrotoluene is mononitrotoluene.

4. A process as defined in claim 2, wherein the nitrotoluene is dinitrotoluene.

5. A process as defined in claim 1, wherein the aromatic compound is a nitrobenzene.

6. A process as defined in claim 1, wherein the acidic solution contains an acid selected from the group consisting of sulfuric acid, nitric acid or mixtures thereof.

7. A process as defined in claim 1, wherein the molten nitrate salt has a melting point of about 70° C.

8. A process as defined in claim 1, wherein the molten nitrate salt is selected from the group consisting of sodium nitrate, potassium nitrate, calcium nitrate hydrate, lithium nitrate hydrate, manganese nitrate hydrate, magnesium nitrate hydrate, zinc nitrate hydrate, or combinations thereof.

9. A process as defined in claim 8, wherein the molten nitrate salt is a combination of magnesium nitrate hydrate and zinc nitrate hydrate.

10. A method as defined in claim 9, wherein the molten nitrate salt is a combination of magnesium nitrate trihydrate and zinc nitrate trihydrate.

11. A process as defined in claim 1, wherein the molten nitrate salt is used in an amount of from about 0.5 to about 1.5 parts, based on the amount of 0.1 part by weight of nitro substituted aromatic compound.

12. A process as defined in claim 1, which is carried out at a temperature of from about 15° C. to about 130° C.

13. A process for separating an acid impurity from a solution containing an acid and nitro toluene, which process comprises:

(a) contacting said solution with at least one molten nitrate salt using from about 0.1 to about 5.0 parts of said nitrate salt per each one part by weight of said nitro substituted aromatic compound while maintaining the temperature of said solution substantially at or above the melting point of said nitrate salt; and (b) removing said acid from said solution.

14. A process as defined in claim 13, wherein the acidic dinitrotoluene solution contains an acid selected from the group consisting of sulfuric acid, nitric acid or mixtures thereof.

15. A process as defined in claim 13, wherein the molten nitrate salt has a melting point of about 70° C.

16. A process as defined in claim 13, wherein the molten nitrate salt is selected from the group consisting of sodium nitrate, potassium nitrate, calcium nitrate hydrate, lithium nitrate hydrate, manganese nitrate hydrate, magnesium nitrate hydrate, zinc nitrate hydrate, or combinations.

17. A process as defined in claim 16, wherein the molten nitrate salt is a combination of magnesium nitrate hydrate and zinc nitrate hydrate.

18. A process as defined in claim 17, wherein the molten nitrate salt is a combination of magnesium nitrate trihydrate and zinc nitrate trihydrate.

19. A process as defined in claim 13, wherein the molten nitrate salt is used in amount of from about 0.5 to about 1.5 parts, based on the amount of 1.0 part by weight of nitro substituted aromatic compound.

20. A process as defined in claim 13, which is carried out at a temperature of from about 15° C. to about 130° C.

21. A process for separating nitric acid from a solution containing nitric acid and nitrotoluene, which process comprises:

(a) contacting said solution with at least one molten nitrate salt using from about 0.1 to about 5.0 parts of said nitrate salt per each one part by weight of said nitro substituted aromatic compound while maintaining the temperature of said solution substantially at or above the melting point of said nitrate salt; and (b) removing said nitric acid from said solution.

22. A process as defined in claim 21, wherein the molten nitrate salt is selected from the group consisting of sodium nitrate, potassium nitrate, calcium nitrate hydrate, lithium nitrate hydrate, manganese nitrate hydrate, magnesium nitrate hydrate, zinc nitrate hydrate, or combinations thereof.

23. A process as defined in claim 22, wherein the molten nitrate salt is a combination of magnesium nitrate hydrate and zinc nitrate hydrate.

24. A process as defined in claim 23, wherein the molten nitrate salt is a combination of magnesium nitrate trihydrate and zinc nitrate trihydrate.

25. A process as defined in claim 21, wherein the nitrotoluene solution after separation of nitric acid contains less than 3% nitric acid.

* * * * *

UNITED STATES PATENT AND TRADEMARK OFFICE
CERTIFICATE OF CORRECTION

PATENT NO. : 5,099,079

DATED : March 24, 1992

INVENTOR(S) : Allen B. Quakenbush

It is certified that error appears in the above-identified patent and that said Letters Patent is hereby corrected as shown below:

At column 5, line 32, please delete "0.1" and insert ---1.0--- in its place.

Signed and Sealed this

Thirteenth Day of July, 1993

Attest:

MICHAEL K. KIRK

*Attesting Officer*  *Acting Commissioner of Patents and Trademarks*